United States Patent
Weeks, Jr.

(10) Patent No.: US 11,590,248 B2
(45) Date of Patent: Feb. 28, 2023

(54) PULSING HIGH INTENSITY NARROW SPECTRUM LIGHT

(71) Applicant: Hubbell Lighting, Inc., Shelton, CT (US)

(72) Inventor: Thomas Warren Weeks, Jr., Simpsonville, SC (US)

(73) Assignee: Hubbell Lighting, Inc., Shelton, CT (US)

( * ) Notice: Subject to any disclaimer, the term of this patent is extended or adjusted under 35 U.S.C. 154(b) by 54 days.

(21) Appl. No.: 16/152,842

(22) Filed: Oct. 5, 2018

(65) Prior Publication Data

US 2019/0125904 A1    May 2, 2019

Related U.S. Application Data

(60) Provisional application No. 62/578,776, filed on Oct. 30, 2017.

(51) Int. Cl.
*A61L 2/26*      (2006.01)
*A61L 2/08*      (2006.01)
(Continued)

(52) U.S. Cl.
CPC ............... *A61L 2/084* (2013.01); *A61L 2/10* (2013.01); *A61L 2/26* (2013.01); *H01J 61/00* (2013.01);
(Continued)

(58) Field of Classification Search
CPC ... A61L 2/084; A61L 2/10; A61L 2/26; A61L 2202/11; A61L 2202/14; A61L 2/08; H01J 61/00; H05B 45/00
See application file for complete search history.

(56) References Cited

U.S. PATENT DOCUMENTS

| | | | |
|---|---|---|---|
| 3,926,556 A | 12/1975 | Boucher | |
| 4,910,942 A | 3/1990 | Dunn et al. | |

(Continued)

FOREIGN PATENT DOCUMENTS

| | | |
|---|---|---|
| JP | 2004301387 | 10/2004 |
| JP | 2007232323 | 9/2007 |

(Continued)

OTHER PUBLICATIONS

Maclean et al., "405 nm light technology lot the inactivation of pathogens and its potential role for environmental disinfection and infection control," *The Journal of Hospital Infection*, Sep. 2014, vol. 88, Issue I—27 pages.

(Continued)

*Primary Examiner* — Balram T Parbadia
(74) *Attorney, Agent, or Firm* — Michael Best & Friedrich LLP

(57) ABSTRACT

Systems and methods for pulsing high intensity narrow spectrum light are provided. In one example embodiment, a lighting system includes can include one or more high intensity narrow spectrum light sources configured to emit high intensity narrow spectrum light. The lighting system can further include a power circuit configured to provide power to the one or more high intensity narrow spectrum light sources and a pulsing circuit configured to control delivery of power to the one or more high intensity narrow spectrum light sources so as to pulse the emission of high intensity narrow spectrum light from the one or more high intensity narrow spectrum light sources.

20 Claims, 7 Drawing Sheets

(51) Int. Cl.
  *A61L 2/10* (2006.01)
  *H01J 61/00* (2006.01)
  *H05B 45/31* (2020.01)
  *H05B 45/325* (2020.01)

(52) U.S. Cl.
  CPC ........ *A61L 2202/11* (2013.01); *A61L 2202/14* (2013.01); *H05B 45/31* (2020.01); *H05B 45/325* (2020.01)

(56) References Cited

U.S. PATENT DOCUMENTS

| | | | |
|---|---|---|---|
| 6,171,548 B1 * | 1/2001 | Rose | A61L 9/20 |
| | | | 422/128 |
| 6,251,127 B1 | 6/2001 | Biel | |
| 8,398,264 B2 | 3/2013 | Anderson et al. | |
| 9,039,966 B2 | 5/2015 | Anderson et al. | |
| 9,333,274 B2 | 5/2016 | Peterson et al. | |
| 9,439,989 B2 | 9/2016 | Lalicki | |
| 9,642,356 B2 | 5/2017 | Wood et al. | |
| 9,642,358 B2 | 5/2017 | Cai et al. | |
| 9,700,641 B2 | 7/2017 | Hawkins et al. | |
| 9,927,097 B2 | 3/2018 | Lalicki et al. | |
| 2002/0074559 A1 | 6/2002 | Dowling et al. | |
| 2002/0161418 A1 * | 10/2002 | Wilkens | H01J 61/125 |
| | | | 607/90 |
| 2003/0137258 A1 | 7/2003 | Piepgras et al. | |
| 2004/0039242 A1 | 2/2004 | Tolkoff et al. | |
| 2004/0141321 A1 | 7/2004 | Dowling et al. | |
| 2005/0049228 A1 | 3/2005 | Albrecht et al. | |
| 2005/0055070 A1 | 3/2005 | Jones et al. | |
| 2005/0107849 A1 | 5/2005 | Altshuler et al. | |
| 2006/0085052 A1 | 4/2006 | Feuerstein et al. | |
| 2006/0221606 A1 | 10/2006 | Dowling et al. | |
| 2008/0137066 A1 | 6/2008 | Weinstein | |
| 2008/0137181 A1 * | 6/2008 | That | H05B 45/00 |
| | | | 359/350 |
| 2009/0076115 A1 | 3/2009 | Wharton et al. | |
| 2009/0168396 A1 | 7/2009 | Moriyasu et al. | |
| 2010/0208054 A1 | 8/2010 | Fan- | |
| 2010/0246169 A1 | 9/2010 | Anderson | |
| 2010/0259917 A1 | 10/2010 | Ramer et al. | |
| 2011/0180687 A1 | 7/2011 | Rains, Jr. et al. | |
| 2011/0227487 A1 | 9/2011 | Nichol et al. | |
| 2011/0256019 A1 | 10/2011 | Gruen et al. | |
| 2012/0126134 A1 * | 5/2012 | Deal | A61L 2/24 |
| | | | 250/372 |
| 2013/0291735 A1 | 11/2013 | Livchak et al. | |
| 2013/0293156 A1 | 11/2013 | Wells | |
| 2013/0330235 A1 * | 12/2013 | Stibich | A61L 2/24 |
| | | | 422/105 |
| 2014/0060096 A1 | 3/2014 | Shur | |
| 2014/0128941 A1 * | 5/2014 | Williams | A61N 5/06 |
| | | | 315/193 |
| 2014/0278136 A1 | 9/2014 | Shamsheyeva et al. | |
| 2014/0303547 A1 * | 10/2014 | Loupis | A61N 5/062 |
| | | | 604/20 |
| 2015/0002027 A1 | 1/2015 | Huang | |
| 2015/0037201 A1 * | 2/2015 | Armour | A61L 2/14 |
| | | | 600/203 |
| 2015/0182646 A1 * | 7/2015 | Anderson | A61L 9/18 |
| | | | 250/492.1 |
| 2015/0231287 A1 * | 8/2015 | Lin | A61M 25/0097 |
| | | | 607/80 |
| 2015/0273092 A1 | 10/2015 | Holub et al. | |
| 2016/0015840 A1 | 1/2016 | Gordon | |
| 2016/0030609 A1 | 2/2016 | Peterson et al. | |
| 2016/0030610 A1 | 2/2016 | Peterson et al. | |
| 2016/0120410 A1 | 5/2016 | Kim | |
| 2016/0339203 A1 | 11/2016 | Krames et al. | |
| 2016/0361229 A1 | 12/2016 | Na | |
| 2016/0375161 A1 | 12/2016 | Hawkins | |
| 2016/0375162 A1 | 12/2016 | Marry | |
| 2016/0375163 A1 * | 12/2016 | Hawkins | F21V 19/006 |
| | | | 422/22 |
| 2017/0000916 A1 * | 1/2017 | Stibich | A61L 2/20 |
| 2017/0006685 A1 | 1/2017 | Barron et al. | |
| 2017/0034889 A1 | 2/2017 | Primous et al. | |
| 2017/0080117 A1 | 3/2017 | Gordon | |
| 2017/0101326 A1 | 4/2017 | Zhou | |
| 2017/0101328 A1 | 4/2017 | Smetona et al. | |
| 2017/0173195 A1 * | 6/2017 | Stibich | A61L 2/24 |
| 2018/0121703 A1 | 5/2018 | Jung | |
| 2018/0225498 A1 | 8/2018 | Setlak | |

FOREIGN PATENT DOCUMENTS

| | | |
|---|---|---|
| WO | WO2007012875 | 2/2007 |
| WO | WO 2009/056838 | 5/2009 |

OTHER PUBLICATIONS

Maclean et al., "An Innovation: Decontamination by Light—HINS-light Environmental Decontamination System, A new method for pathogen control in the clinical environment," Microsoft Power Point, HINS-light EDS Presentation for Infection Prevention Scotland, The Robertson Trust Laboratory for Electronic Sterilisation Technologies (ROLEST), Oct. 27, 2010—20 pages.

Noimark et al., "Light-activated antimicrobial surfaces with enhanced efficacy induced by a dark-activated mechanism," Chemical Science, Issue 6, Jun. 1, 2014—1 page.

Wallace, John "HINS light kills surface bacteria in hospitals," Laser Focus World, http://www.laserfocusworld.com/articles/2010/11/hins-light-kills-surface.html, accessed on Oct. 30, 2017, PennWell Corporation, Tulsa, OK, Nov. 15, 2010—2 pages.

Maclean et al., Environmental decontamination of a hospital isolation room using high-intensity narrow-spectrum light, The Hospital Infection Society, Elsevier Ltd., Nov. 2010;76(3)—1 page.

Kenali Mfg. Launches New Bacteria-killing LED Light for Hospitals, LEDinside, a Business Division of TrendForce Corp., Jun. 29, 2015. accessed on Oct. 30, 2017, http://www.ledinside.com/products/2015/6/kenall_manufacturing_launches_new_uv_led_light_for_hospitals—3 pages.

Nitzan et al. "ALA induced photodynamic effects on Gram positive and negative bacteria," *Photochem. Photobiol. Sci.*, 2004, 3—18 pages.

MACLEAN "An Investigation Into The Light Inactivation Of Medically Important Microorganisms," University of Strathclyde, 2006—260 pages.

Nitzan et al., "Endogenous Porphyrin Production in Bacteria by Aminolaevulinic Acid and Subsequent Bacterial Photoeradication," *M. Lasers Med Sci* (Dec. 1999) vol. 14, Issue 4, pp. 269-277.

Ashkenazi et al., "Eradication of Propionibacterium acnes by its endogenous porphyrins after illumination with high intensity blue light," *FEMS Immunology & Medical Microbiology*, vol. 35, Issue 1, Jan. 1, 2003, pp. 17-24.

Ganz et al., "*Helicobacter pylori* in Patients Can Be Killed by Visible Light," *Lasers Surg Med.*, Apr. 2005; 36(4): pp. 260-265.

Møller et al., "How Finsen's light cured lupus vulgaris," *Photodermatol Photoimmunol Photomed* 2005; 21: pp. 118-124.

Kjeldstad, "Photoinactivation of Propionibacterium acnes by Near-Ultraviolet Light," *Zeitschrift für Naturforschung C*, vol. 39, Issue 3-4, 1984, pp. 300-302.

Derosa et al., "Photosensitized singlet oxygen and its applications," *Coordination Chemistry Reviews*, vols. 233-234, Nov. 1, 2002, pp. 351-371.

Elman et al., "The effective treatment of acne vulgaris by a high-intensity, narrow band 405-420 nm light source," *J Cosmetic & Laser Ther* 2003; 5: pp. 111-116.

Konig et al., "Red Light Kills Bacteria via Photodynamic Action," ABSTRACT, *Cellular and molecular biology*, 46(7):1297-303, Dec. 2000—1 page.

(56) References Cited

OTHER PUBLICATIONS

Philipp-Dormston et al., "Comparison of Porphyrin and Heme in Various Heterotrophic Bacteria," ABSTRACT, *Enzyme* 16(1):57-64 • Feb. 1973—1 page.

* cited by examiner

PULSING HIGH INTENSITY NARROW SPECTRUM LIGHT

PRIORITY CLAIM

The present application is based on and claims priority to U.S. Provisional Application 62/578,776 having a filing date of Oct. 30, 2017, which is incorporated by reference herein.

FIELD

The present subject matter relates generally to lighting systems.

BACKGROUND

Lighting systems can be used to provide illumination of spaces and objects for a variety of different applications. In some lighting systems, high intensity narrow spectrum (HINS) light can be used to reduce, suppress, and/or inactivate bacterial or other microorganisms. For instance, HINS light having a peak wavelength in the range of about 380 nanometers (nm) to about 420 nm (e.g., 405 nm) has been shown to inactivate certain microorganisms, such as certain gram-positive bacteria.

SUMMARY

Aspects and advantages of embodiments of the present disclosure will be set forth in part in the following description, or may be learned from the description, or may be learned through practice of the embodiments.

One example aspect of the present disclosure is directed to a lighting system. The lighting system can include one or more high intensity narrow spectrum light sources configured to emit high intensity narrow spectrum light. The lighting system can further include a power circuit configured to provide power to the one or more high intensity narrow spectrum light sources and a control circuit configured to control delivery of power to the one or more high intensity narrow spectrum light sources so as to pulse the emission of high intensity narrow spectrum light from the one or more high intensity narrow spectrum light sources.

Other example aspects of the present disclosure are directed to systems, methods, devices, circuits and apparatus for pulsing high intensity narrow spectrum light.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which.

DETAILED DESCRIPTION

Figure 1:
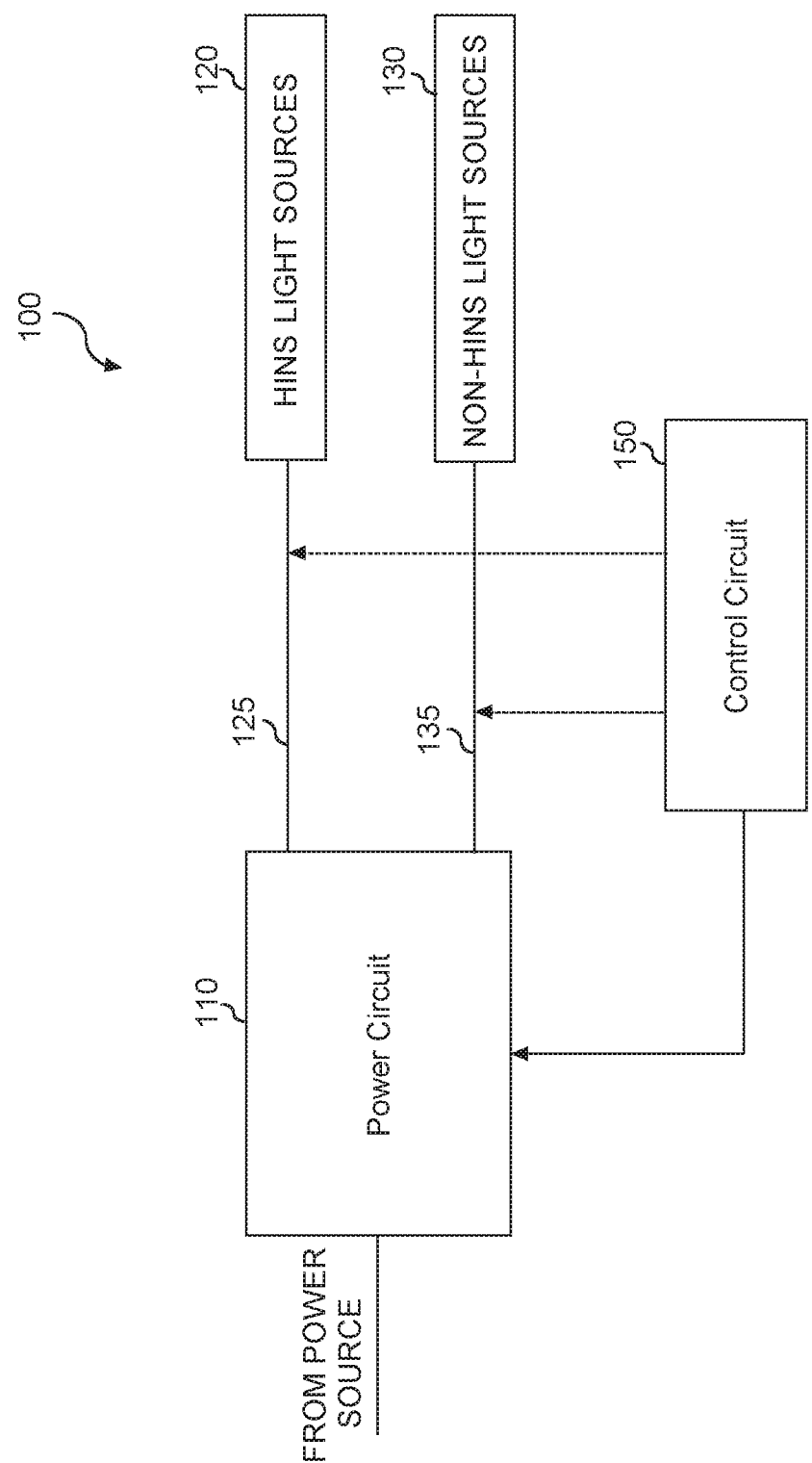
FIG. 1 depicts an overview of an example lighting system according to example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Example aspects of the present disclosure are directed to systems and methods for pulsing high intensity narrow spectrum (HINS) light. A lighting system can be used to illuminate a space or surface with HINS light for a variety of purposes, including antimicrobial purposes. The HINS light can include, for instance, light having a peak wavelength in the range of about 380 nanometers (nm) to about 420 nm, such as about 400 nm to about 420 nm, such as about 405 nm. As will be understood by those skilled in the art, using the disclosures provided herein, HINS light can provide antimicrobial qualities to surfaces upon which the light is emitted. In this manner, the HINS light can reduce, eliminate, suppress and/or inactivate bacterial, fungal, viral, and/or other microorganism contamination on such surfaces.

According to example aspects of the present disclosure, a lighting system can be configured to illuminate a space and/or surface with pulsed HINS light. The pulsed HINS light can be used, for instance, for antimicrobial purposes (e.g., to reduce, eliminate, suppress, or inactive bacterial, fungal, viral, and/or other microorganism contamination on various surfaces or in various spaces). In some implementations, the pulsed HINS light can be combined with other wavelengths of light, for instance through electroluminescence or photoluminescence, to create visible white light.

Pulsing HINS light can provide for higher intensity dosing of spaces and/or surfaces with HINS light over shorter durations. In this way, a high dosage of HINS light does not have to be applied continuously to achieve antimicrobial effects. In some cases, faster antimicrobial effects can be obtained using high intensity pulsed dosing versus lower intensity continuous dosing of HINS light. Indeed, in some cases, continuous dosing of HINS light may not even be necessary to achieve antimicrobial effects depending on the absorption of HINS light and rate of chemical reactions within microorganisms exposed to the HINS light. As a result, pulsed application of HINS light according to example aspects of the present disclosure can facilitate faster decontamination with less application of HINS light, leading to more efficient operation of a lighting system.

In some example embodiments, a lighting system can include one or more HINS light sources configured to emit HINS light. The HINS light sources can include a light emitting diode (LED) light sources configured to emit light having a peak wavelength in the range of about 380 nanometers (nm) to about 420 nm, such as about 400 nm to about 420 nm, such as about 405 nm. The LED light sources can emit light as a result of electrons moving through a semiconductor material. The LED light sources can include various coatings, lens, materials, etc. to provide for the emission of HINS light. In some implementations, the one or more HINS light sources can be used with light sources configured to emit other wavelengths of light to create visible white light.

The lighting system can include a power circuit to provide power to the HINS light sources. The lighting system can include, for instance, a driver circuit configured to convert an AC power to a DC power suitable for powering the one or more HINS light sources. The lighting system can further include a control circuit configured to control application of power to the HINS light sources so as to pulse HINS light. For instance, the control circuit can control the driver circuit to pulse the application of power to the one or more HINS light sources. As another example, the control circuit can control one or more switching elements coupled between a driver circuit and the one or more HINS light sources to provide for the pulsing of HINS light. Other suitable control techniques can be used to control the delivery of power to the one or more HINS light sources so as to pulse the emission of HINS light without deviating from the scope of the present disclosure.

In some example embodiments, the power applied to the HINS light sources can be controlled to pulse the HINS light according to a pulsing scheme. The pulsing scheme can specify one or more pulses of HINS light at periodic, regular intervals or irregular intervals. Each pulse can each be associated with an intensity (e.g. magnitude). Each pulse can be associated with a duration (e.g., pulse width). In some embodiments, the intensity and/or duration can be selected to achieve antimicrobial results (e.g., based on a required dosing time to deactivate certain microorganisms). In some embodiments, the intensity and/or duration can be selected such that the pulsing of the HINS light occurs at a frequency that is not visible or detectable by humans.

As used herein, a lighting system can include, but is not limited to, one or more of a lighting circuit, light engine, one or more luminaires, one or more lighting fixtures, one or more lighting units, a plurality of lighting devices arranged in an environment, a combination of any of the foregoing, etc. HINS light refers to light having a peak wavelength in the range of about 380 nanometers (nm) to about 420 nm, such as about 400 nm to about 420 nm, such as about 405 nm. Non-HINS light refers to light in the visible spectrum, but not in the HINS range of 380 nm to 405 nm. As used herein, the use of the term "about" in conjunction with a numerical value refers to within 2.5% of the stated numerical value.

One example aspect of the present disclosure is directed to a lighting system. The lighting system includes one or more high intensity narrow spectrum (HINS) light sources configured to emit HINS light. The lighting system includes a power circuit configured to provide power to the one or more HINS light sources. The lighting system includes a control circuit configured to control delivery of power to the one or more HINS light sources so as to pulse the emission HINS light from the one or more HINS light sources. The HINS light can have a wavelength in the range of about 380 nm to about 420 nm, such as about 405 nm.

In some embodiments, the control circuit is configured to control delivery of power to the one or HINS light sources to pulse the emission of HINS light according to a pulsing scheme. The pulsing scheme specifies one or more pulses for emission of HINS light. Each of the one or more pulses having a duration and intensity. In some embodiments, the duration and intensity of each pulse can be selected for antimicrobial purposes. For instance, in some embodiments, the duration of each pulse can be about 8 microseconds or less. In some embodiments, a frequency of pulses is about 120 Hz or greater.

In some embodiments, the pulsing scheme includes a first pulse and a second pulse. The first pulse can be associated with a first time period and the second pulse can be associated with a second time period. The first pulse and the second pulse can be separated by a third time period. The third time period can be greater than the first time period and the second time period, such as at least an order of magnitude greater (e.g., 10 times greater) than the first time period.

In some embodiments, the pulsing scheme comprises a saw tooth pulsing scheme, such as a decaying saw tooth pulsing scheme. In some embodiments, the pulsing scheme specifies that HINS light is pulsed from a steady state intensity.

In some embodiments, the one or HINS light sources can include one or more light emitting diodes (LEDs). The power circuit can include a driver circuit. The control circuit can be configured to control a switching element coupled between the driver circuit and the one or more LEDs to pulse the emission of HINS light.

Another example aspect of the present disclosure is directed to a method of controlling one or more high intensity narrow spectrum (HINS) lighting sources. The method can include providing, by one or more power circuits, power to one or more HINS lighting sources. The method can include obtaining, by one or more control circuits, data indicative of a pulsing scheme. The method can include controlling, by the one or more control circuits, power provided by the one or more power circuits to the one or more HINS lighting sources based at least in part on the data indicative of the pulsing scheme so as to pulse the emission of HINS light from the one or more HINS lighting sources.

In some embodiments, the pulsing scheme specifies one or more pulses for emission of HINS light. Each of the one or more pulses having a duration and intensity. In some embodiments, the duration and intensity of each pulse can be selected for antimicrobial purposes. For instance, in some embodiments, the duration of each pulse can be about 8 microseconds or less. In some embodiments, a frequency of pulses is about 120 Hz or greater.

In some embodiments, the pulsing scheme includes a first pulse and a second pulse. The first pulse can be associated with a first time period and the second pulse can be associated with a second time period. The first pulse and the second pulse can be separated by a third time period. The third time period can be greater than the first time period and the second time period, such as at least an order of magnitude greater (e.g., 10 times greater) than the first time period.

In some embodiments, the pulsing scheme comprises a saw tooth pulsing scheme, such as a decaying saw tooth pulsing scheme. In some embodiments, the pulsing scheme specifies that HINS light is pulsed from a steady state intensity.

FIG. 1 depicts an overview of an example lighting system 100 according to example embodiments of the present disclosure. The lighting system 100 includes a power circuit 110, one or more HINS light sources 120, and a control circuit 150. Optionally, the lighting system 100 can include one or more non-HINS light sources 130.

The power circuit 110 can receive AC or DC power from a power source and can convert the power to a power suitable for illuminating HINS light sources 120. The power from the power circuit 110 can be provided to the HINS light sources 120 over a suitable channel 125 (e.g., one or more conductors, circuit paths, traces, etc.). Optionally, power can be provided from the power circuit 110 to one or more non-HINS light sources 130 over a suitable channel 135 (e.g., one or more conductors, circuit paths, traces, etc.)

The one or more HINS light sources 120 can be any light sources configured to emit HINS light. As discussed in detail below, in example implementations, the HINS light sources 120 include one or more LED light sources. The present disclosure is discussed with reference to LED light sources for example purposes. Other types of light sources configured to emit HINS light, can be used as HINS light sources 120 without deviating from the scope of the present disclosure.

The one or more non-HINS light sources 130 can be any light sources configured to emit non-HINS light. The one or more non-HINS light sources 130 can be used to emit light to be combined with HINS light to create visible white light of a desired color temperature or visual effect. As discussed in detail below, in example implementations, the non-HINS light sources 120 include one or more LED light sources. Other types of light sources configured to emit non-HINS light, can be used as non-HINS light sources 130 without deviating from the scope of the present disclosure.

The control circuit 150 can be configured to control the power circuit 110 and/or the channel 125 so as to pulse the emission of HINS light from the HINS light sources 120. For instance, the control circuit 150 can send lighting control signals to the power circuit to pulse power provided over channel 125 to the HINS light sources 120. In addition and/or in the alternative, the control circuit 150 can control the channel 125 (e.g., one or more switching elements disposed in the channel) to pulse power provided to the HINS light sources 120 so as to pulse the emission of HINS light from the HINS light sources 120.

In some embodiments, the control circuit 150 can be configured to control the power circuit 110 and/or the channel 135 to pulse the emission of non-HINS light from the non-HINS light sources 130. For instance, the control circuit 150 can send lighting control signals to the power circuit to pulse power provided over channel 135 to the non-HINS light sources 130. In addition and/or in the alternative, the control circuit 150 can control the channel 135 (e.g., one or more switching elements disposed in the channel) to pulse power provided to the non-HINS light sources 130 so as to pulse the emission of non-HINS light from the non-HINS light sources 130.

The control circuit 150 and other control circuits disclosed herein can include a microcontroller, microprocessor and one or more memory devices, one or more logic devices, one or more application specific integrated circuits, a control interface, a control system, or other suitable device or circuit that can be provide control functionality according to aspects of the present disclosure. The control circuit 150 can be implemented as part of the same module (e.g., on the same circuit board) or separate from the power circuit 110. In some embodiments, the control circuit 150 can be remote from power circuit 110 and can provide control signals to the power circuit 110 and/or the channels 125, 135 over a suitable communication medium (e.g., wireless communication medium, wired communication medium, etc.) using any suitable protocol (e.g., 0-10V, DALI, DMX, 802.11, Ethernet protocol, USB protocols, etc.)

According to example aspects of the present disclosure, the control circuit 150 can control the power circuit 110 and/or the channel 125 (e.g., switching elements in the channel) to pulse the emission of HINS light from the HINS light sources 130 according to a pulsing scheme. The pulsing scheme can be specified by an operator of the system using a suitable user interface and/or can be programmed (e.g., pre-programmed) into one or more memory devices accessible by the control circuit 150. Example pulsing schemes will be discussed in detail with reference to FIGS. 4-9.

Figure 2:
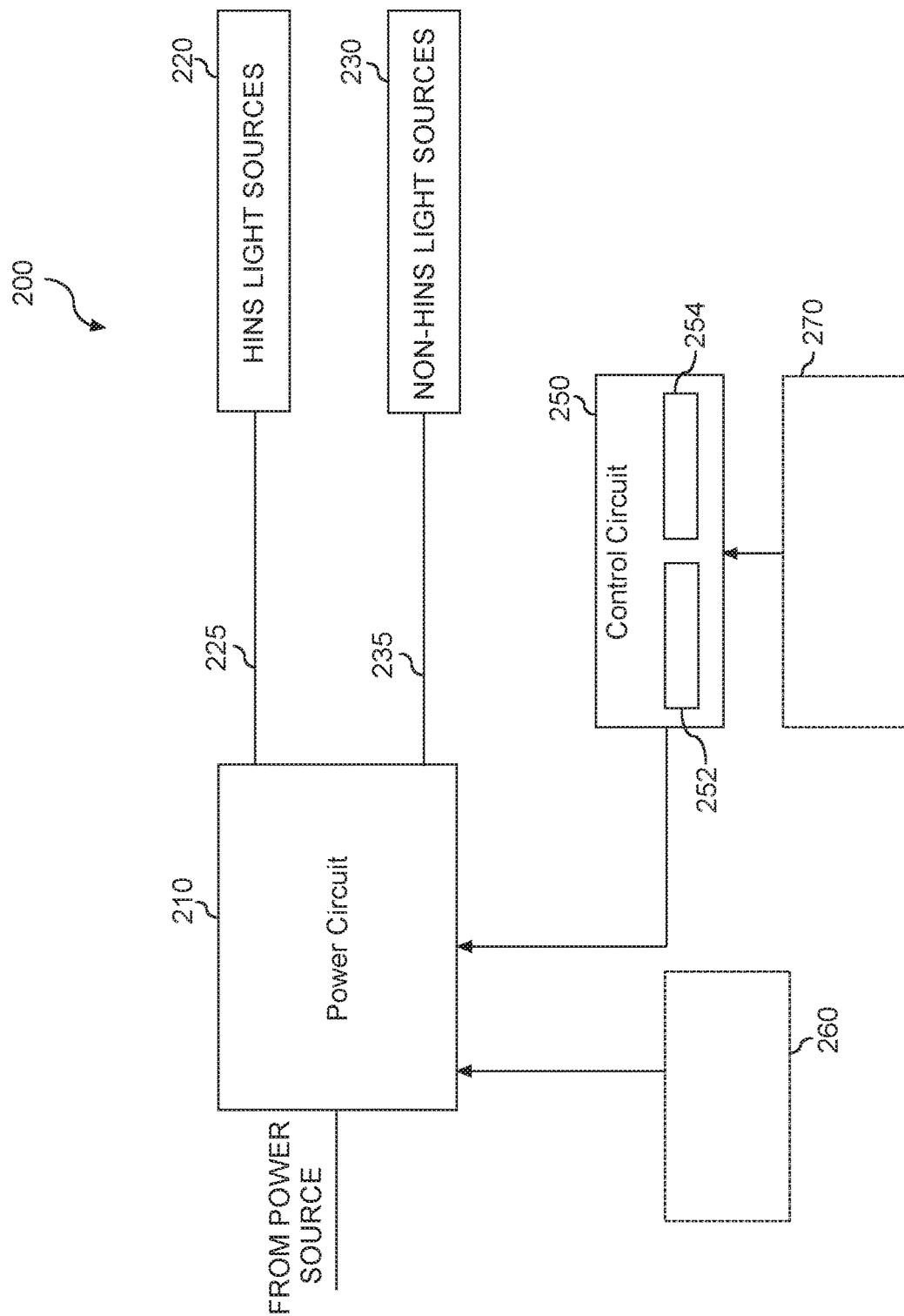
FIG. 2 depicts an example LED lighting system according to example embodiments of the present disclosure.

FIG. 2 depicts an example implementation of an LED lighting system 200 configured to pulse HINS light according to example aspects of the present disclosure. The LED lighting system 200 includes an LED driver circuit 210, a control circuit 250, and one or more HINS LEDs 220 (e.g., a HINS LED array) configured to emit HINS light. The LED lighting system 200 can optionally include one or more non-HINS LEDs 230 (e.g., a non-HINS LED array) configured to emit non-HINS light. The lighting system can include other light sources without deviating from the scope of the present disclosure.

The HINS LEDs 220 can include can include one or more LED devices. The LED devices can emit light as a result of electrons moving through a semiconductor material. The LED devices can be configured to emit HINS light or can include one or more coatings, lenses, materials, etc. that transform light emitted by the LED devices into HINS light. The non-HINS LEDs 230 can include one or more LED devices. The LED devices can be configured to emit non-HINS light of any suitable color and/or color temperature. The HINS LEDs 220 and the non-HINS LEDs 230 can be implemented on the same circuit board or on different circuit boards.

The driver circuit 210 can be, for instance, any suitable driver circuit 210 configured to convert an input power (e.g., an input AC or DC power) to a suitable driver output (e.g. driver current) for powering the HINS LEDs 220 and the non-HINS LEDs 230. In some embodiments, the driver circuit 210 can be a dimmable driver circuit. The driver circuit 210 is illustrated as a multichannel driver circuit configured to power HINS LEDs 220 over a first channel 225 and to power non-HINS LEDs 230 over a second channel 235. Other suitable arrangements can be used to provide power to the HINS LEDs 220 and non-HINS LEDs 230 without deviating from the scope of the present disclosure. For instance, independent driver circuits can be used to power the HINS LEDs 220 and the non-HINS LEDs 230. As another example, a current splitter circuit can be used to allocate driver current between HINS LEDs 220 and non-HINS LEDs 230.

In some embodiments, the dimmable driver circuit 210 can include various components, such as switching elements (e.g. transistors) that are controlled to provide a suitable driver output. For instance, in some example embodiments, the driver circuit 210 can include one or more transistors. Gate timing commands can be provided to the one or more transistors to convert the input power to a suitable driver output using pulse width modulation techniques. In some example embodiments, the dimmable driver circuit 210 can be a line dimming driver, such as a phase-cut dimmable driver, Triac dimmer, trailing edge dimmer, or other line dimming driver. The driver output can be adjusted using the line dimming driver by controlling the input power to the dimmable driver circuit 210.

In some embodiments, an interface 260 can be provided at the driver circuit 210 for receiving a dimming control signal used to control the driver output. The interface 260 can include one or more components for communicating a dimming control signal to the driver circuit 210. For example, the interface 260 can include one or more circuits, terminals, pins, contacts, conductors, or other components for communicating a dimming control signal to the driver circuit 210.

The dimming control signal can be provided from an external circuit, such as an external dimming circuit or external control device. The external circuit can include one or more devices, such as a smart dimming interface, a potentiometer, a Zener diode, or other device. In some embodiments, the dimming control signal can be received from the control circuit 250. In one example implementation, the dimming control signal can be a 0V to 10V dimming control signal. The dimming control signal can be implemented using other suitable protocols, such as a DALI protocol, or a DMX protocol.

The control circuit 250 can be configured to control the delivery of power to the HINS LEDs 220 from the driver circuit 210 so as to pulse the emission of HINS light from the HINS LEDs 220. For example, the control circuit 250 can control the driver output provided over channel 225 so as to pulse power to the HINS LEDs so that the emission of light by the HINS LEDs 220 is pulsed according to a pulsing scheme. Example pulsing schemes will be discussed in detail with reference to FIGS. 4-6. The control circuit 250 can be configured to control the delivery of power to the non-HINS LEDs 230 in any suitable manner to provide a desired light output of the lighting system 200.

As illustrated, the control circuit 250 can include one or more processors 252 and one or more memory devices 254. The one or more memory devices 254 can store computer-readable instructions that when executed by the one or more processors 252 cause the one or more processors to provide control functionality according to example aspects of the present disclosure. For instance, the one or more memory devices 254 can store computer-readable instructions that when executed by the one or more processors 252 cause the control circuit 250 to pulse the emission of light by the HINS LEDs 230 according to a pulsing scheme. The pulsing scheme can be pre-programmed into the memory devices 254 or may be programmed by a user from time-to-time in one or memory devices 254 using a suitable user interface.

The control circuit 250 can be implemented on the same circuit board as the driver circuit 210 or can be located remote from the driver circuit 210 and/or the HINS LEDs 230. In some embodiments, the control circuit 250 can control the driver circuit 210 over a suitable communication medium, such as a wired or wireless communication medium.

In some embodiments, the control circuit 250 can include an interface 270 for receiving a lighting control signal. The interface 270 can include one or more components for communicating the lighting control signal to the control circuit 250. For example, the interface 270 can include one or more circuits, terminals, pins, contacts, conductors, or other components for communicating the lighting control signal.

The lighting control signal, in some embodiments, can be and/or include data indicative of a pulsing scheme (e.g., can include data or other information used to determine an appropriate pulsing scheme). The control circuit 250 can be configured to control the driver circuit 210 to provide for pulsing emission of HINS light from the HINS LEDs 220 based on the lighting control signal.

In some embodiments, the lighting control signal can be provided from an external circuit, such as an external control device. The external circuit can include one or more devices, such as a smart control interface or other device. In one example implementation, the lighting control signal can be a 0V to 10V dimming control signal. The lighting control signal can be implemented using other suitable protocols, such as a DALI protocol, or a DMX protocol.

Figure 3:
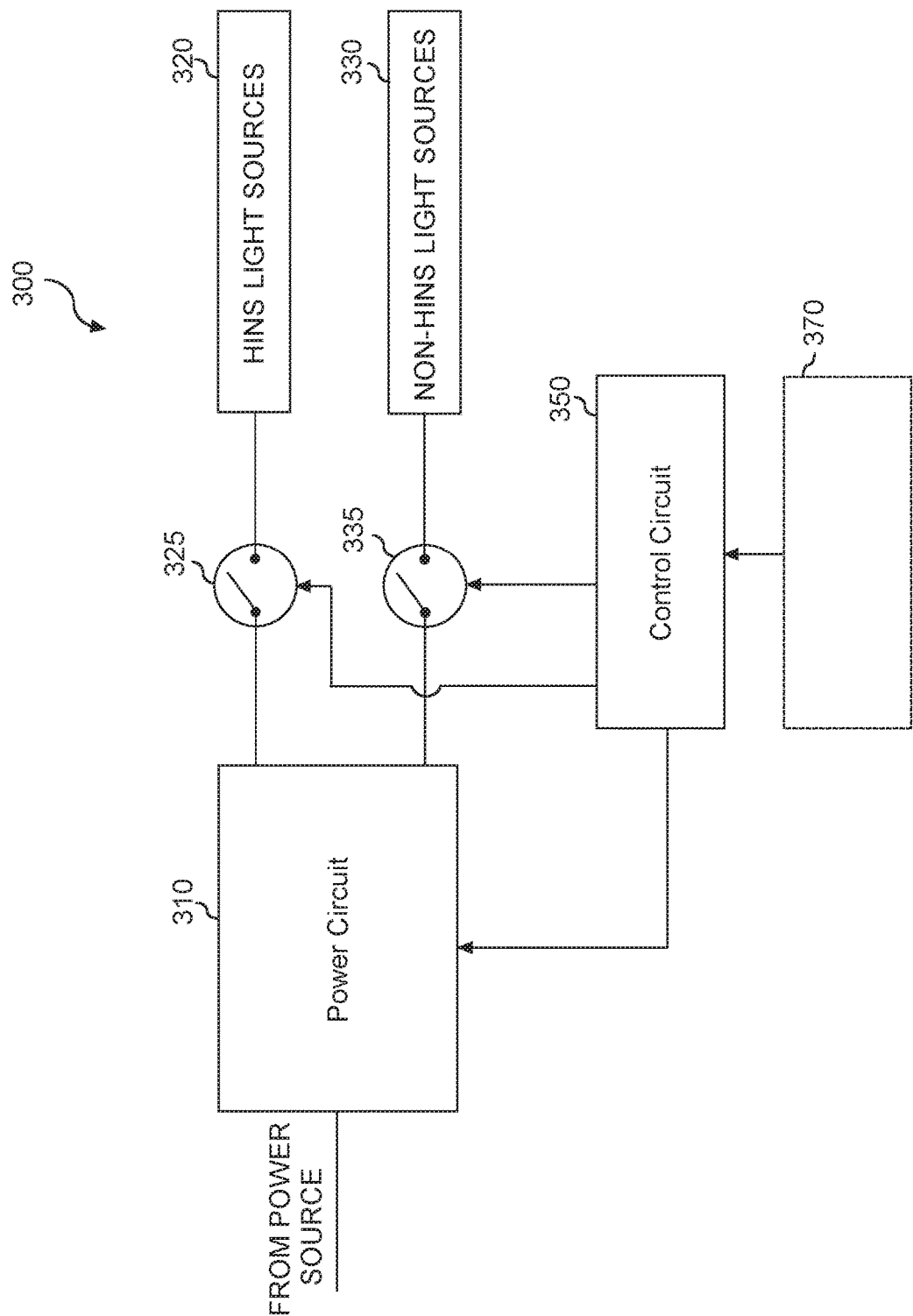
FIG. 3 depicts an example LED lighting system according to example embodiments of the present disclosure.

FIG. 3 depicts an example implementation of an LED lighting system 300 configured to pulse HINS light according to example aspects of the present disclosure. The LED lighting system 300 includes an LED driver circuit 310, a control circuit 350, and one or more HINS LEDs 320 (e.g., a HINS LED array) configured to emit HINS light. The LED lighting system 300 can optionally include one or more non-HINS LEDs 330 (e.g., a non-HINS LED array) configured to emit non-HINS light. The lighting system can include other light sources without deviating from the scope of the present disclosure.

The HINS LEDs 320 can include one or more LED devices. The LED devices can emit light as a result of electrons moving through a semiconductor material. The LED devices can be configured to emit HINS light or can include one or more coatings, lenses, materials, etc. that transform light emitted by the LED devices into HINS light. The non-HINS LEDs 330 can include one or more LED devices. The LED devices can be configured to emit non-HINS light of any suitable color and/or color temperature. The HINS LEDs 320 and the non-HINS LEDs 330 can be implemented on the same circuit board or on different circuit boards.

The driver circuit 310 can be, for instance, any suitable driver circuit 310 configured to convert an input power to a suitable driver output for power the HINS LEDs 320 and the non-HINS LEDs 330. In some embodiments, the driver circuit 310 can be a dimmable driver circuit. The dimmable driver circuit 310 can be configured to receive an input power, such as an input AC power or an input DC power, and can convert the input power to a suitable driver output (e.g. driver current) for powering the HINS LEDs 320 and/or the non-HINS LEDs 2330. The driver circuit 210 is illustrated as a multichannel driver circuit configured to power HINS LEDs 220 over a first channel 2325 and to power non-HINS LEDs 230 over a second channel 335. Other suitable arrangements can be used to provide power to the HINS LEDs 320 and non-HINS LEDs 330 without deviating from the scope of the present disclosure.

The control circuit 350 can be configured to control the delivery of power to the HINS LEDs 320 from the driver circuit 310 so as to pulse the emission of HINS light from the HINS LEDs 320 by controlling a switching element 325 coupled between the driver circuit 310 and the HINS LEDs 320. For example, the control circuit 350 can control the switching element 325 so as to pulse power to the HINS LEDs so that the emission of light by the HINS LEDs 220 is pulsed according to a pulsing scheme. Example pulsing schemes will be discussed in detail with reference to FIGS. 4-9. The control circuit 350 can be configured to control a switching element 335 to control power to the non-HINS LEDs 230 in any suitable manner to provide a desired light output of the lighting system 200.

The switching element 325 can be any suitable switching element. In some embodiments, the switching element 325 can be a switching element such as a transistor (e.g., BJT, MOSFET, IGBT, etc.). The control circuit 350 can control the switching element by providing control signals (e.g., gate commands) to the switching element 325. In some embodiments, the switching element 325 can be a relay or other suitable device configured to interrupt power to the HINS LEDs 320 based on control signals from the control circuit 350.

The switching element 335 can be any suitable switching element. In some embodiments, the switching element 335 can be a switching element such as a transistor (e.g., BJT, MOSFET, IGBT, etc.). The control circuit 350 can control the switching element by providing control signals (e.g., gate commands) to the switching element 335. In some embodiments, the switching element 325 can be a relay or other suitable device configured to interrupt power to the non-HINS LEDs 330 based on control signals from the control circuit 350.

The control circuit 350 can include one or more processors and one or more memory devices. The one or more memory devices can store computer-readable instructions that when executed by the one or more processors cause the one or more processors to provide control functionality according to example aspects of the present disclosure. For instance, the one or more memory devices can store computer-readable instructions that when executed by the one or more processors cause the control circuit to pulse the emission of light by the HINS LEDs according to a pulsing scheme. The pulsing scheme can be pre-programmed into the memory devices or may be programmed by a user from time-to-time in one or memory devices using a suitable user interface.

The control circuit 350 can be implemented on the same circuit board as the driver circuit 310 or can be located remote from the driver circuit 310 and/or the HINS LEDs 330. In some embodiments, the control circuit 350 can control the switching element 325 over a suitable communication medium, such as a wired or wireless communication medium.

In some embodiments, the control circuit 350 can include an interface 370 for receiving a lighting control signal. The interface 370 can include one or more components for communicating the lighting control signal to the control circuit 350. For example, the interface 370 can include one or more circuits, terminals, pins, contacts, conductors, or other components for communicating the lighting control signal.

The lighting control signal, in some embodiments, can be indicative of a pulsing scheme. The control circuit 350 can be configured to control the switching element 325 to provide for pulsing emission of HINS light from the HINS LEDs 330 based on the lighting control signal.

In some embodiments, the lighting control signal can be provided from an external circuit, such as an external control device. The external circuit can include one or more devices, such as a smart control interface or other device. In one example implementation, the lighting control signal can be a 0V to 10V dimming control signal. The lighting control signal can be implemented using other suitable protocols, such as a DALI protocol, or a DMX protocol.

Figure 4:
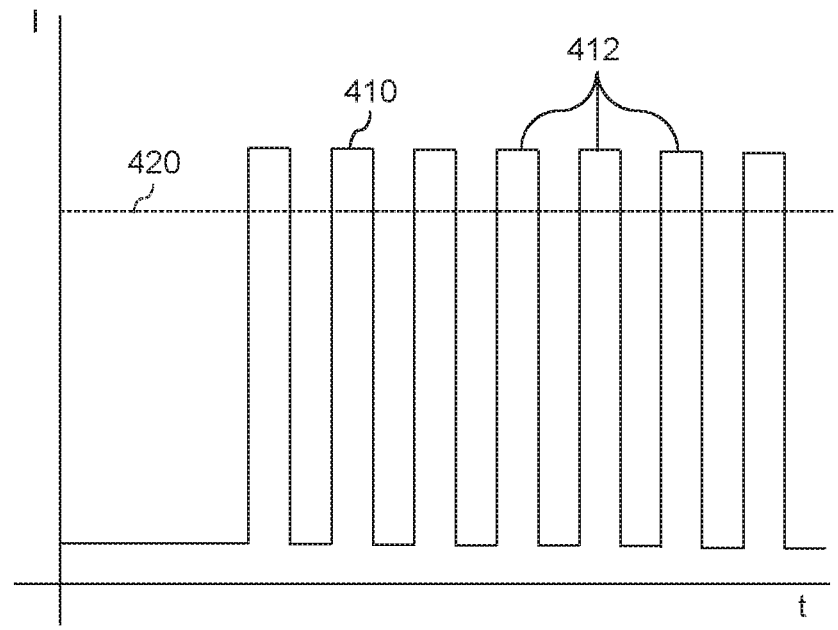
FIG. 4 depicts an example pulsing scheme according to example embodiments of the present disclosure.

FIG. 4 depicts a graphical representation of an example pulsing scheme for the emission of HINS light according to example embodiments of the present disclosure. FIG. 4 plots time along the horizontal axis and HINS light intensity along the vertical axis.

Curve 410 represents a pulsing scheme according to example embodiments of the present disclosure. As shown, the pulsing scheme includes a plurality of pulses 412 of HINS light. The pulses 412 are provided at regular intervals according to a specified frequency. In some embodiments, the frequency can be selected such that the pulsing of HINS light is not detectable by the human eye. For instance, the frequency can be about 120 Hz or greater.

Figure 5:
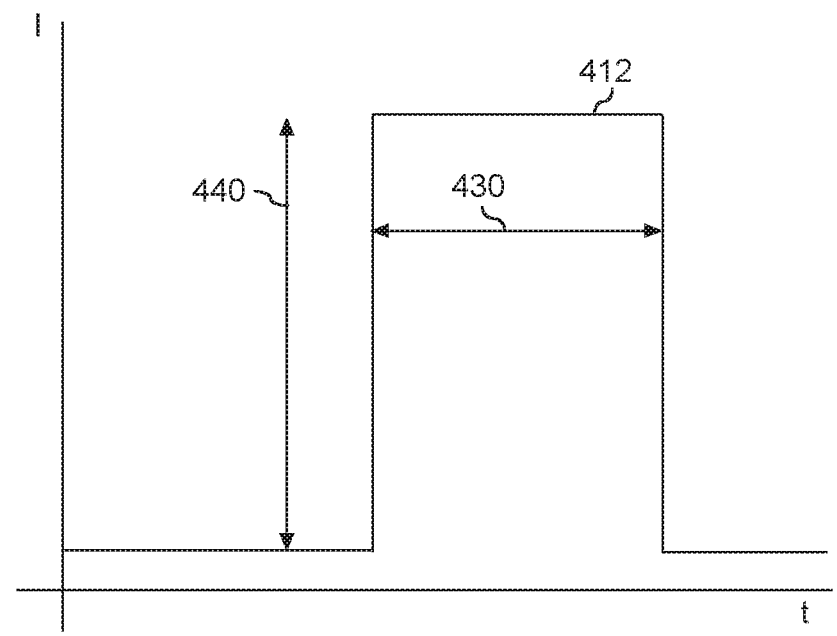
FIG. 5 depicts an example pulse according to example embodiments of the present disclosure.

FIG. 5 depicts a graphical representation of on example pulse 412 from the pulsing scheme 410 of FIG. 4. FIG. 5 plots time along the horizontal axis and HINS light intensity along the vertical axis.

As shown, pulse 412 includes a pulse width 430 (e.g., duration) and a magnitude 440. The pulse 412 is illustrated as a square pulse. Other suitable pulse shapes can be used without deviating from the scope of the present disclosure. In some embodiments, the pulse width 430 and/or the magnitude 440 can be selected based on characteristics of various microorganisms (e.g., gram-positive bacteria) to deactivate the microorganism. For instance, the pulse 412 can have a pulse width 430 and a magnitude 440 sufficient to allow a microorganism to absorb the HINS light for deactivation or other antimicrobial purposes. In some embodiments, the pulse width 430 can be, for instance, in the range of about less than about 1 microsecond to about 500 microseconds, such as about 1 microsecond to about 100 microseconds, such as about 5 microseconds to about 20 microseconds.

In some embodiments, the magnitude 440 associated with a pulse 412 can be greater than a magnitude or intensity associated with a continuous dosing of HINS light. For example, FIG. 4 illustrates a curve 420 representative of a continuous dosing of HINS light. As shown, the intensity associated with the pulses 412 of the pulsing scheme are greater than an intensity associated with continuous dosing 420. In this way, a space or surface can be exposed to HINS light with higher intensity within a shorter period of time.

Figure 6:
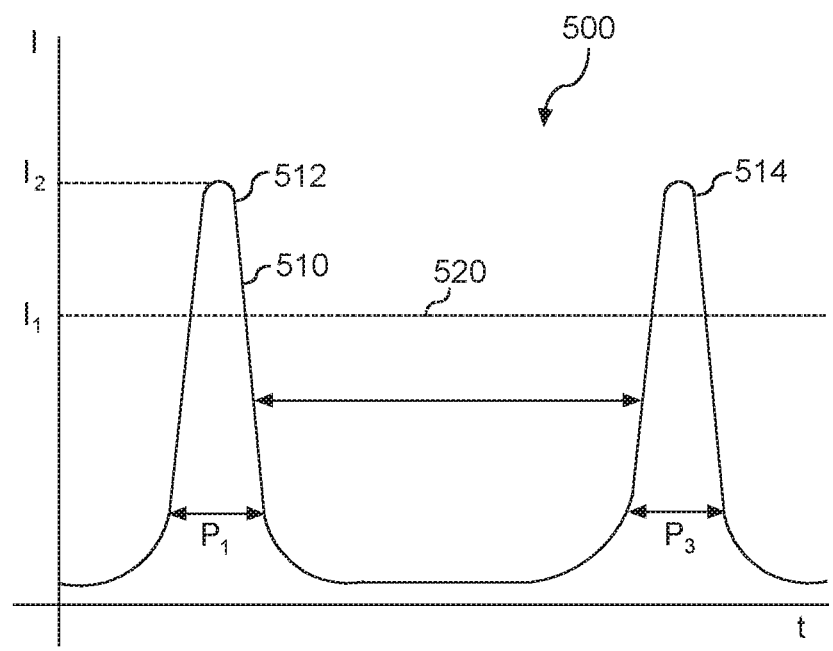
FIG. 6 depicts an example pulsing scheme according to example embodiments of the present disclosure.

FIG. 6 depicts a graphical representation of a pulsing scheme 500 according to example embodiments of the present disclosure. FIG. 5 plots time along the horizontal axis and HINS light intensity along the vertical axis.

The pulsing scheme 500 includes a plurality of pulses, including pulse 512 and pulse 514. Pulse 512 and pulse 514 are each associated with an intensity $I_1$. Pulse 512 has a duration $P_1$. Pulse 514 has a duration $P_3$. $P_1$ can be different from or the same as $P_3$. Pulse 512 and pulse 514 can be separated by a time period $P_2$.

In some embodiments, the time period $P_2$ can be significantly greater, such one or more orders of magnitude greater than the time periods $P_1$ and $P_3$. For example, time periods $P_1$ and $P_2$ can be a few seconds and time period $P_3$ can be several minutes or even hours.

In some embodiments, the intensity $I_1$ associated with pulses 512 and 514 can be significantly greater than an intensity associated with a continuous dosing of HINS light. For instance, curve 520 represents an example continuous dosing of HINS light at an intensity $I_2$. The intensity $I_2$ can be such that the continuous dosing of HINS light provides an antimicrobial effect on a surface (e.g., deactivates certain microorganisms). $I_1$ can be significantly greater, such as at least two times greater, such as at least five times greater, such as at least ten times greater than $I_2$ so that antimicrobial effects can be provided in a shorter period of time of illumination of HINS light relative continuous dosing of HINS light.

Example pulsing schemes for pulsing HINS light are disclosed in FIGS. 4-6 for purposes of illustration and discussion. Those of ordinary skill in the art, using the disclosures provided herein, will understand that other pulsing schemes and/or combinations of pulsing schemes can be used in a variety of different manners without deviating from the scope of the present disclosure.

Figure 7:
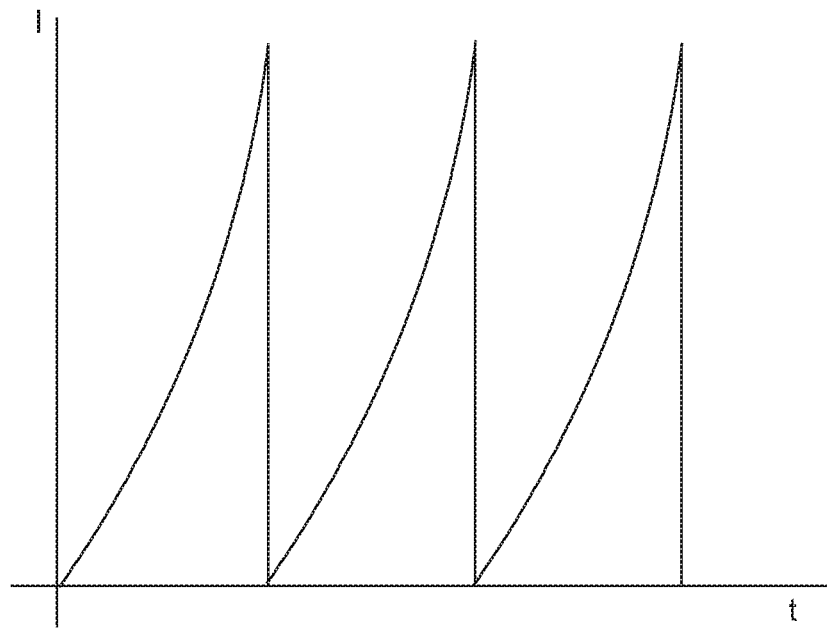
FIG. 7 depicts an example pulsing scheme according to example embodiments of the present disclosure.
Figure 8:
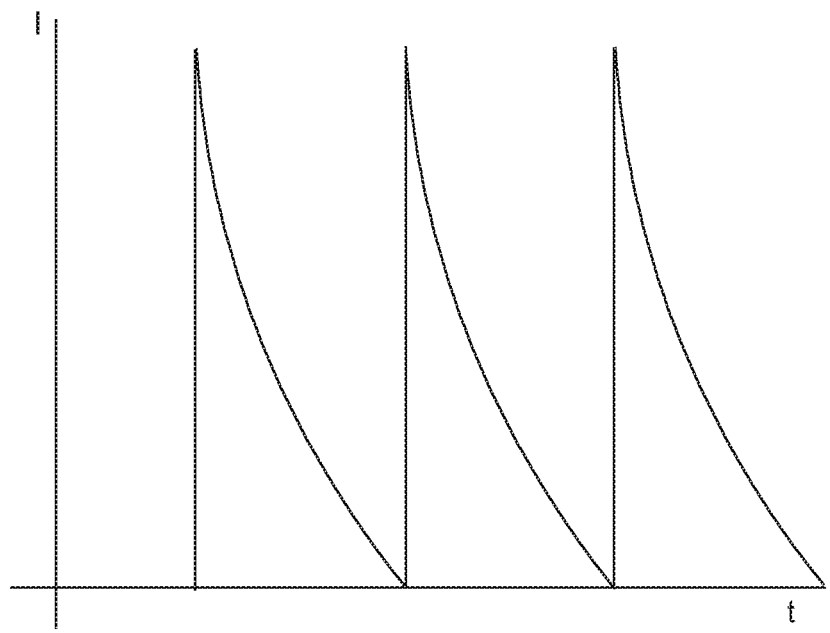
FIG. 8 depicts an example pulsing scheme according to example embodiments of the present disclosure.
Figure 9:
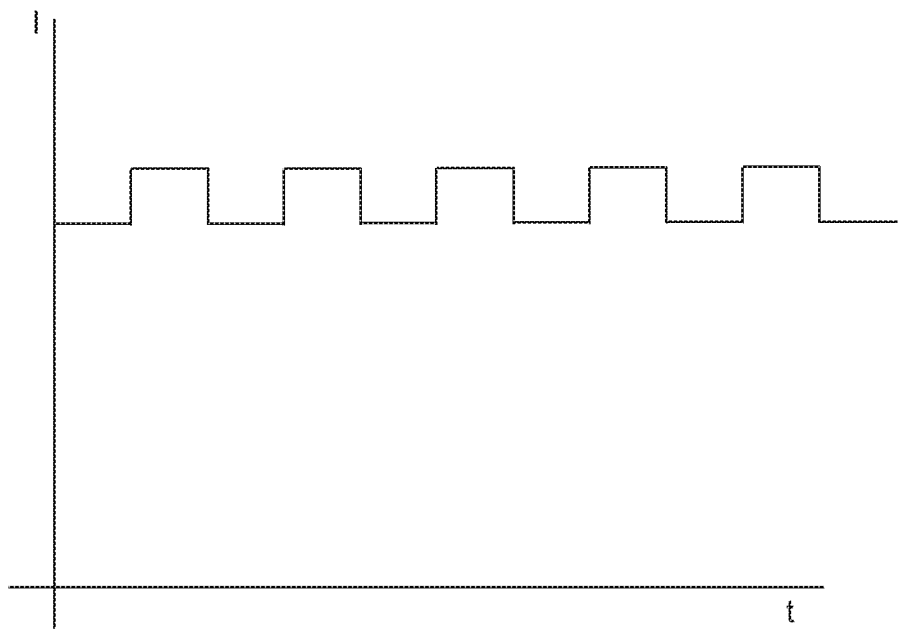
FIG. 9 depicts an example pulsing scheme according to example embodiments of the present disclosure.

For instance, FIG. 7 depicts an example saw tooth pulsing scheme according to example embodiments of the present disclosure. FIG. 8 depicts an example decaying saw tooth pulsing scheme according to example embodiments of the present disclosure. FIG. 9 depicts an example pulsing scheme where HINS light is pulsed from a constant steady state intensity (e.g., non-zero intensity) as opposed to from zero intensity.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A lighting system, comprising:
   one or more high intensity narrow spectrum (HINS) light sources configured to emit HINS light;
   one or more non-HINS light sources configured to emit non-HINS light in the visible spectrum;
   a power circuit configured to provide power to both the one or more HINS light sources and the non-HINS light sources;
   a control circuit configured to control delivery of power to the one or more HINS light sources and the one or more non-HINS light sources to pulse the emission of light according to a pulsing scheme the pulsing scheme comprising a first pulse and a second pulse, the first pulse associated with a first duration and a first intensity and the second pulse associated with a second duration and a second intensity,
   wherein the first duration and the second duration are different durations,
   wherein both the first pulse and the second pulse of the pulsing scheme are applied to one HINS light selected from the one or more HINS lights, and selectively cause the one HINS light selected from the one or more HINS lights to emit HINS light according to the pulsing scheme, and
   wherein the one or more non-HINS lights emits non-HINS light in the visible spectrum independently of the one or more HINS lights.

2. The lighting system of claim 1, wherein the HINS light has a wavelength in the range of about 380 nm to about 420 nm and the non-HINS light is in the visible spectrum and not in the range of 380 nm to 405 nm.

3. The lighting system of claim 1, wherein the HINS light has a wavelength of about 405 nm.

4. The lighting system of claim 1, wherein the pulsing scheme specifies one or more pulses for emission of HINS light, each of the one or more pulses having a duration and intensity.

5. The lighting system of claim 4, wherein the duration and intensity of each pulse is selected for antimicrobial purposes.

6. The lighting system of claim 4, wherein the duration of each pulse is about 8 microseconds or less.

7. The lighting system of claim 4, wherein a frequency of pulses is about 120 Hz or greater.

8. The lighting system of claim 4, wherein the pulsing scheme comprises a saw tooth pulsing scheme.

9. The lighting system of claim 4, wherein the pulsing scheme specifies that HINS light is pulsed from a steady state intensity.

10. The lighting system of claim 4, wherein the one or HINS light sources comprise one or more light emitting diodes (LEDs).

11. The lighting system of claim 10, wherein the power circuit comprises a driver circuit, wherein the control circuit is configured to control a switching element coupled between the driver circuit and the one or more LEDs to pulse the emission of HINS light.

12. The lighting system of claim 1, wherein the first pulse and the second pulse are separated by a third time period, the third time period being greater than the first duration and the second duration.

13. The lighting system of claim 12, wherein the third time period is at least an order of magnitude greater than the first duration.

14. The lighting system of claim 1, wherein the HINS light and the non-HINS light are combined in accordance with the pulsing scheme to create visible white light.

15. The lighting system of claim 1 wherein the first intensity and the second intensity are different intensities.

16. A method of controlling one or more high intensity narrow spectrum (HINS) lighting sources and one or more non-HINS lighting sources, the method comprising:
    providing, by one or more power circuits a multichannel driver circuit having a first channel and a second channel, power to one or more of the HINS lighting sources and the non-HINS lighting sources;
    obtaining, by one or more control circuits, data indicative of a pulsing scheme, the pulsing scheme comprising a first pulse and a second pulse, the first pulse associated with a first duration and a first intensity and the second pulse associated with a second duration and a second intensity, wherein the first duration and the second duration are different durations;
    controlling, by the one or more control circuits, power provided by the one or more power circuits to the one or more HINS lighting sources and the non-HINS lighting sources based at least in part on the data indicative of the pulsing scheme so as to pulse the emission of HINS light from the one or more HINS lighting sources,
    wherein both the first pulse and the second pulse of the pulsing scheme are applied to one HINS light selected from the one or more HINS lights, and configured to selectively cause the one HINS light selected from the one or more HINS lights to be emitting HINS light for at least part of a period during which non-HINS light in the visible spectrum is being emitted and not emitting HINS light for at least part of the period during which non-HINS light in the visible spectrum is being emitted.

17. The method of claim 16, wherein the first and second duration is about 8 microseconds or less.

18. The method of claim 16, wherein the pulsing scheme specifies a frequency of pulses of about 120 Hz or greater.

19. The method of claim 16, wherein the pulsing scheme comprises a first pulse and a second pulse, the first pulse associated with a first duration and the second pulse associated with a second duration, the first pulse and the second pulse being separated by a third time period, the third time period being greater than the first time period and the second time period.

20. The method of claim 16, wherein the HINS lighting sources and the non-HINS lighting sources are disposed on a single circuit board.

\* \* \* \* \*